United States Patent [19]

Pusinelli et al.

[11] Patent Number: 5,512,046
[45] Date of Patent: Apr. 30, 1996

[54] DOSING DEVICE FOR THE VOLUMETRIC DOSING OF A LIQUID ADDITIVE

[75] Inventors: Thomas Pusinelli, Altenstadt; Dieter Mushoff, Lich, both of Germany

[73] Assignee: Fresenius AG, Bad Homburg, Germany

[21] Appl. No.: 343,861

[22] Filed: Nov. 17, 1994

[30] Foreign Application Priority Data

Nov. 23, 1993 [DE] Germany .......................... 43 39 811.1

[51] Int. Cl.$^6$ .................................................. A61M 31/00
[52] U.S. Cl. .............................. 604/465; 604/67; 604/84; 604/4
[58] Field of Search .................................... 604/4, 65–67, 604/81.83

[56] References Cited

U.S. PATENT DOCUMENTS

| Re. 33,021 | 8/1989 | Danby | 604/80 |
|---|---|---|---|
| 4,231,366 | 11/1980 | Schael | 604/4 |
| 4,451,255 | 5/1984 | Bujan et al. | 604/157 |
| 5,234,403 | 8/1993 | Yoda et al. | 604/4 |

FOREIGN PATENT DOCUMENTS

| 0189491 | 8/1986 | European Pat. Off. . |
|---|---|---|
| 0361662 | 4/1990 | European Pat. Off. . |
| 0438703 | 12/1990 | European Pat. Off. . |
| 0568265 | 11/1993 | European Pat. Off. . |
| 2361580 | 12/1973 | Germany . |
| 3910992A1 | 4/1989 | Germany . |

OTHER PUBLICATIONS

"Intraoperative Autotransfusion", The American Journal of Surgery, vol. 123, 1972 pp. 257–259.

Primary Examiner—Randall L. Green
Assistant Examiner—Mark O. Polutta
Attorney, Agent, or Firm—Henderson & Sturm

[57] ABSTRACT

A dosing device for volumetric dosing of a liquid additive which is added in a certain volume ratio to a fluid, in particular withdrawn blood, flowing in a first hose line, via a second hose line feeding directly or indirectly into the first hose line. The dosing device for the volumetric dosing of an anticoagulant fluid or a sedimentation accelerator is preferably provided in a system for the collection and retransfusion of autologous blood which has a hose or tube section which extends downstream from the junction, and also a drip chamber connecting downstream from the drip tube and a light barrier, the direction of action of which is arranged transversely to the fall path of the drops. In order to avoid incorrect dosing because of changing viscosities of the liquid flowing in the first hose line, and thus of changing drop sizes, two electrically-triggerable valve means, one of which is in each case inserted into one of the two hose lines, are provided. The valve means are triggered alternately by means of a counting and control unit in such a way that in each case only one of the two named hoses is switched to "open" at the same time. The liquid remaining in the drip tube as a result of capillary action thereby brings about a volume constancy between drops falling at the lower end of the drip tube and additive which is added at the upper end of the drip tube.

11 Claims, 2 Drawing Sheets

DOSING DEVICE FOR THE VOLUMETRIC DOSING OF A LIQUID ADDITIVE

BACKGROUND OF THE INVENTION

1. Field of the Invention

The present invention relates to a dosing device for the volumetric dosing of a liquid additive which is added in a certain volume ratio to a fluid flowing in a first hose line via a second hose line which feeds directly or indirectly into the first hose line. The dosing device of the present invention includes a hose or tube section, which is called a drip tube, which extends downstream from the junction, and has a drip chamber connecting downstream from the drip tube and a light barrier. The direction of action of the light barrier is arranged transversely to the fall path of the drops. Such a dosing device is used in particular within a system for the collection and retransfusion of autologous blood in order to add an anticoagulant liquid or a sedimentation accelerator to blood drawn, or sucked-off and intended for retransfusion, for example during an operation or similar.

2. Discussion of Background and/or Material Information

A system for the collection and retransfusion of autologous blood is, for example, known from EP-OS 0 483 703. In the known system, a collection vessel is subjected to an underpressure which is used, by means of a hose attached to the collecting vessel, to suck off blood from an operative field, i.e. from the body of a patient. The sucked-off blood, which is called drainage blood, flows through the hose line and passes a quantity dosing device before it drips into the collection container. Arranged upstream of the quantity dosing device is a Y-shaped branching or junction into which a second hose feeds which is connected to a reservoir for an anticoagulant liquid and/or a sedimentation accelerator. Situated between the reservoir for the anticoagulant liquid and the Y-shaped branching is a valve means which can be triggered via the previously mentioned quantity dosing device.

Conventional dosing devices, known from the prior art, operate according to the principle of drop counting, whereby the fluid which flows in a tube and is to be measured or monitored, is guided to a drip chamber which is surrounded by a light barrier. A drop of liquid falling in the drip chamber breaks the light beam from the light barrier and so generates a counting pulse which can be fed to a microprocessor or similar means for further evaluation. It is a disadvantage with this type of volume measurement of a flowing liquid that, the greater the viscosity fluctuations experienced by the liquid to be measured, the more inaccurate is the measured result. The reason for this is that changing kinematic tenacity, i.e. viscosity, and changing density bring with them a change in the volume of an individual drop. As it is only the absolute number of fallen drops which can be determined by the light barrier, this leads the actual volumetric mixture ratio to change when a certain volume of additive is added to a certain number of fallen drops, for example, by a signal being generated by the quantity dosing device after a certain number of fallen drops, ascertained by means of the light barrier, by means of which the valve means arranged in the hose line and connected to the reservoir of the anticoagulant liquid is triggered and opened for a certain time interval.

On the other hand, the principle of volume determination by means of a drip chamber and light barrier is cheap and easy to put into practice and operates, at least as far as the light barrier component is concerned, without contact, which, in particular in the case of systems and devices which process blood of patients, is highly desirable for reasons of hygiene.

SUMMARY OF INVENTION

It is, therefore, the object of the invention to improve a dosing device of a generic type for the volumetric dosing of a liquid additive which is to be added, as described, in a certain volume ratio to a fluid, in particular blood, flowing in a first hose line, via a second hose line which feeds directly or indirectly into the first hose line in such a way that, despite the use of a drip chamber and a light barrier for drop-counting and, therefore, indirect volume determination of the fluid flowing in the first hose line, a metered addition of the additive to be added, in particular of an anticoagulant liquid, is made possible in a fixed volume ratio, without the dosing being falsified by changing viscosities of the liquid flowing in the first hose line.

The realization of this object is characterized in the case of a generic dosing device by two controllable valves or valve means which are each inserted into one of the two hose lines and coupled in such a way that in each case only one of the two valve means can be switched to "open" at a certain time point, and also by a counting and control unit which counts the drops falling through the drip chamber and after a certain number of drops triggers the valve means alternately.

The present invention is based at least in part on the knowledge that, because of the capillary action, a certain volume of fluid always remains in the section of the first hose line which leads to the drip chamber, which can optionally also be formed in the shape of a tube and which is called a drip tube.

If the second hose line, conveying the additive to be added, is connected by means of the valve means in such a way that additive can flow into the drip tube and if, at the same time, the first hose line is blocked by the other valve means, the volume of additive advancing into the drip tube corresponds to the volume of the drop leaving the drip tube. If, now, the mixture ratio between additive and primary fluid, for example blood, is expressed in integral multiples of drops, for example one drop of additive per seven drops of blood, a change in viscosity and a changed size of an individual drop resulting therefrom thus has no influence on the overall mixture ratio, since, for example in the case of a larger drop leaving the drip tube, a larger quantity of additive is correspondingly drawn into the drip tube.

In a preferred embodiment or version of the present invention, the two valve means are combined to give a 4/2-way valve. The 4/2-way valve is preferably provided with a spring pre-tension, so that the valve in its at-rest position switches the first hose line to "open" and the second hose line, conveying the additive, is blocked. In the engaged state the situation is then reversed so that the first hose line is blocked and the second hose line is freed.

In another preferred embodiment or version of the present invention the valve means are combined to give a 3/2-way valve, so that the second hose line in the valve feeds indirectly into the first hose line. To put it another way, the connections of the 3/2-way valve are connected such that the first hose line in the spring-centered resting position of the valve is connected directly to the drip tube, while the second hose line conveying the additive is blocked. In the connected state, the situation is again reversed so that the second hose line, conveying the additive, is now directly connected to the drip tube and the first hose line is blocked.

In another alternative or variant of the present invention, which is somewhat more expensive in terms of circuitry, it is proposed to combine the valve means in a 3/3-way valve which has a spring-centered middle position in which both hose lines are blocked. This additional position offers the advantage that both hose lines can be blocked, for example if a collection vessel catching the drawn-off blood is to be replaced.

In another preferred embodiment or version of the present invention, the counting and control unit of the dosing device includes a central processing unit (CPU) and also a freely programmable memory (RAM), and also inputting means in order to enter a value N representing a number of drops. The central processing unit (CPU) generates a control pulse for the alternate triggering of the valve means if the determined number of drops reaches the value N stored in the memory (RAM). Through the possibility of choice for the value N, the operator is offered the opportunity of setting the volumetric mixture ratio in which the additive is to be added.

Also preferred is an embodiment or a version of the dosing device according to the present invention in which the counting and control unit has a freely programmable memory (RAM) in which is provided a storage location for a constant (A) which corresponds to the number of drops of additive to be added per switching cycle of the valve means. Through the possibility of choice for the value A there is provided another possibility of influencing the mixture ratio and setting the device to different additives.

It has also proved to be advantageous for the counting and control unit of the present invention to have a central processing unit (CPU) and a freely programmable memory (RAM) in which an operating program for the processing unit is stored which controls the valve means alternately in such a way that, after a certain number of switching cycles of the valve means, a so-called "test switching cycle" is carried out in which the second hose line conveying the additive is connected through until it is ensured that the second hose line or the reservoir connected to the second hose line still contains a supply of additive. For this purpose, a large enough quantity of drops is admitted in the engaged position of the valve so that the volume of additive which has flown out, as recorded by the light barrier, corresponds to the volume of the drip tube and dead spaces possibly contained in the valve means in any case, even if only very small drops should fall because of viscosity influences.

It is also preferably provided that the dosing device of the present invention contains disposable parts which are disposed of after use or contamination with blood. These individual components listed as parts which can be disposed of can include in particular the two hose lines, the two valve means, the drip tube and the drip chamber. In this way, an hygienically acceptable manageable device is provided in which the expensive components, such as the light barrier and the counting and control unit, which are not subjected to dirt or wear, are retained, while the parts coming into contact with blood can be replaced quickly and easily, which is very much in keeping with a quick and efficient handling in particular in hospitals.

In order to simplify exchangeability, in particular of a drip chamber constructed as a disposable part, the drip chamber and the light barrier can be preferably constructed so that the drip chamber can be locked in the appropriately constructed light barrier. This is preferably effected if the drip chamber is lockable in a form-locking manner in the component containing the light barrier, i.e. a recess is provided in the housing of the light barrier in which the drip chamber, which is partially transparent, can be locked. The drip chamber can in particular be manufactured from a plastic by injection moulding.

The invention is described in more detail below with reference to two preferred embodiments shown in the drawings.

DETAILED DESCRIPTION

Figure 1:
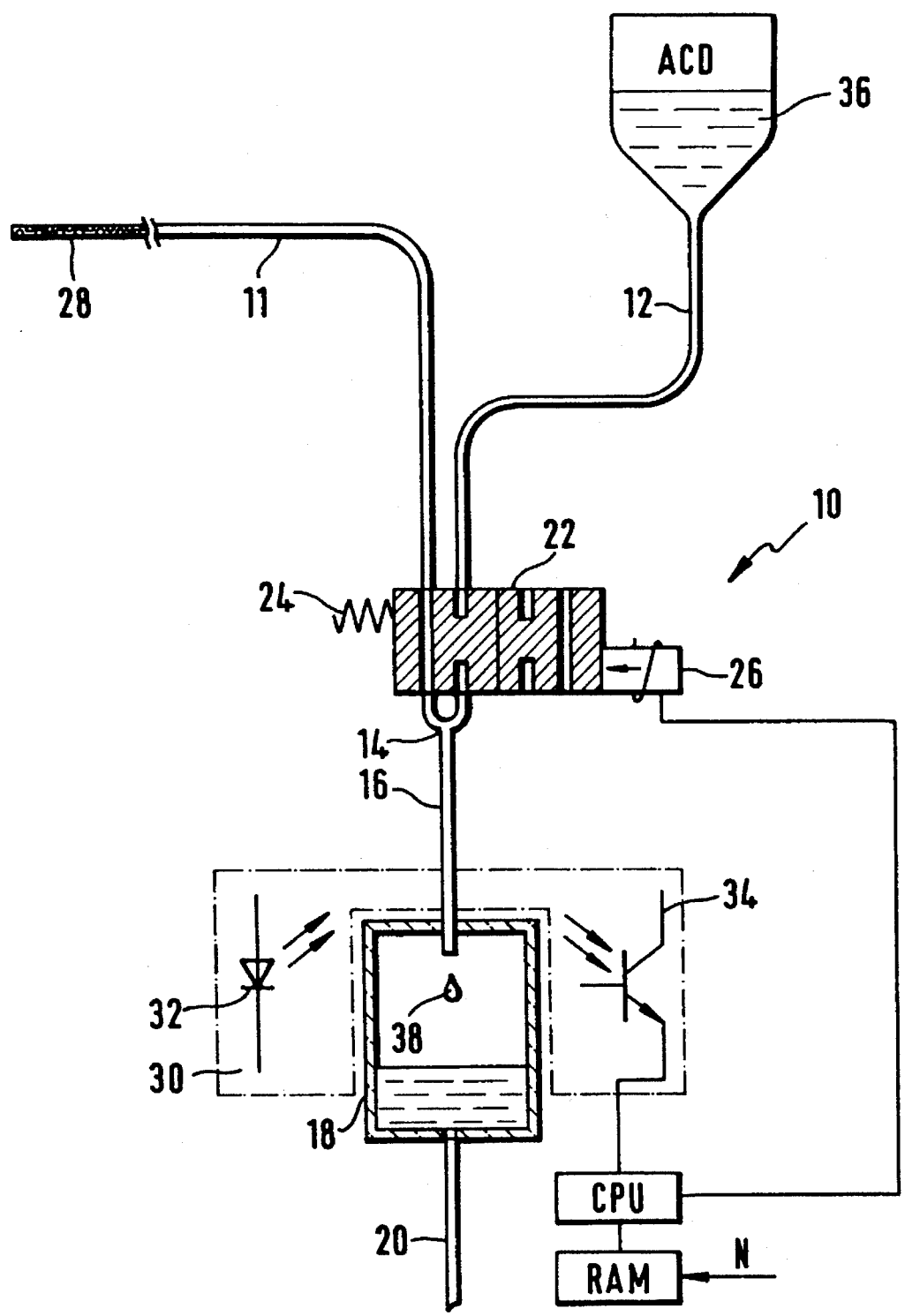
FIG. 1 is a schematic representation of a first version.

The embodiment or version of a dosing device according to the present invention which is shown in FIG. 1 is given the general reference number 10. It has a first hose line 11 and a second hose line 12. The two hose lines 11 and 12 meet at a Y-shaped junction 14 and pass into a drip tube 16. Connected to the drip tube is a drip chamber 18 which is subjected to an underpressure or vacuum via a draw-off or vacuum line 20. Inserted into the two hose lines 11 and 12 are combined valve means in the form of a 4/2-way valve 22. The 4/2-way valve is held by means of a compression spring 24 in a resting position, in which the first hose line 11 is switched to "open" while the second hose line 12 is blocked. The 4/2-way valve 22 can be operated electrically by means of a solenoid 26 so that, in the switch position then adopted, the first hose line 11 is blocked while the second hose line 12 is connected to the drip tube 16.

In the situation shown in FIG. 1, in which the valve 22 is in the resting position, the first hose line 11 is switched to "open". The lower pressure or vacuum acting in the drip chamber 18, which is achieved via the vacuum or draw-off line 20, acts via the drip tube 16 and the valve 22 into the hose line 11 which has a perforated end-section 28. The end-section 28 of the hose line 11 is, for example, placed in an opening in the body, such as an operation wound, and as described herein, withdraws or sucks off blood and/or wound fluid. The withdrawn or sucked-off blood is conveyed through the hose line 11 and the valve 22, which is switched to "open", and drops at the end of the drip tube 16 into the drip chamber 18.

The descending drops break the light beam, emitted transversely to the drip direction, of a light barrier 30 which is constructed to surround the drip chamber. The light barrier 30 is constructed in traditional manner and includes for example a light-emitting diode (LED) 32 as the light source, and as the receiver element a phototransistor 34. The phototransistor 34 illuminated by the light diode 32 is darkened by a falling drop 38, as a result of which a pulse is generated which is fed to a central processing unit (CPU). In the processing unit the pulses generated by the descending drops 38 are added together and compared with a set value N stored in a freely programmable memory (RAM). The desired set value can, for example, be 7. After 7 drops have fallen a control pulse is generated by the central processing unit (CPU) which is conveyed in a suitably amplified manner to the solenoid 26 of the valve 22, whereupon the valve engages and blocks the hose line 11, while, however, releasing the hose line 12. Arranged at the upper end of the hose line 12 is a reservoir 36 which contains an anticoagulant liquid (ACD) and optionally other additions of a sinking accelerator which increases the volume of the erythrocyte aggregates contained in the blood and thus accelerates sedimentation, i.e. separation of blood plasma and optionally contained wound fluid, lymph water, or the like.

The hose line 12 is connected via the now-opened valve 22 directly to the drip tube 16 which is still filled with blood at this point in time due to the capillary action. As soon as another drop 38 falls at the lower end of the drip tube 16, a corresponding volume of anticoagulant liquid (ACD) is drawn up from the hose line 12 at the upper end of the drop tube via the switched-through valve 22. As the volume replaced at the upper end of the drip tube corresponds exactly to the volume which has been discharged in drop form at the lower end of the drip tube, the size of the drop leaving the drip tube has no influence on the mixture ratio, which for example in the present example is 7:1 in parts by volume.

After another descending drop 38 has been detected by means of the light barrier and the central processing unit (CPU), the CPU generates another control pulse, with which the exciting current of the solenoid 26 is switched off, whereupon the compression spring 24 presses the 4/2-way valve into its resting position so that the hose line 11 is switched to "open" and further blood is drawn through the drainage hose 11.

In order to ensure that the reservoir 36 for the anticoagulant liquid is still filled, the switch valve 22 should be kept in the engaged position, after a certain number of switch changes, for the duration of a descending drop 38. The valve should also be kept in the engaged position, switching through the hose line 12, for a number of descending drops which is measured such that the total volume of the falling drops is slightly greater than the internal volume of the drip tube 16 plus possible dead spaces in the valve 22. In these ways it can be ensured that anticoagulant fluid is still contained in the reservoir 36.

To control this routine, a suitable program controlling the CPU can be stored in the memory (RAM).

In order to counter an increased concentration of the anticoagulant liquid in the blood, which would result because of such a metered addition of anticoagulant liquid for test purposes, the value N can be increased for the normal switching cycles accordingly, so that the overall mixture ratio between blood and anticoagulant liquid in the collection vessel, which connects to the drip chamber, again corresponds to the originally intended mixture ratio after a finite number of switching cycles of the valve despite the additional input of anticoagulant fluid during the "test cycle".

For this purpose, the determining influencing variable is the number of drops which is necessary to measure a volume which is certainly greater than the volume of the drip tube plus the volume of possible dead spaces in the valve 22. This is the case even in the most unfavourable situation where the smallest conceivable drop size is produced. This is due at least in part to the fact that, for example, the viscosity of the blood has an unfavourable influence. A drop which falls over and above this number or value N shows that ACD is still present.

This number or value N also can be influenced through the dimensioning of the drip tube. Furthermore, the number of switching cycles which are passed through before a "test switching cycle" is undertaken is variable. In a test switching cycle the switch valve 22 remains in the engaged position longer than only for one falling drop, i.e. with switched-through anticoagulant liquid line 12.

If, for example, a mixture ratio of 7:1 is desired, with a normal rhythm, i.e. without test cycle, the valve 22 will remain in the resting position for seven descending drops 38 and then switches into the engaged position for one drop.

If one now assumes that every tenth switching cycle is to be a test switching cycle, during which a total of eleven drops fall through the drip chamber while anticoagulant liquid is drawn through the valve 22 located in the engaged position, then the number of drops which fall while the switching valve is in the resting position at that time, i.e while the hose line 11 is switched to "open", is to be increased to fourteen. After ten complete switching cycles, a total of one hundred and forty drops of blood have then advanced into the drip tube, while, during the nine normal switching cycles, nine drops of anticoagulant liquid have been added and, in the tenth switching cycle, eleven drops of anticoagulant liquid. The overall mixture ratio is therefore 140:20, i.e 7:1, as without the test switching cycle.

Because of readily comprehensible relationships, other numerical proportions which allow the use of a described test switching cycle without changing the mixture ratio can be found by appropriately dimensioning the drip tube or the number of normal switching cycles or the mixture ratios. Experience shows that a changing drop size resulting from changing viscosities does not influence the mixture ratio.

For purposes of the invention, the drip chamber 18 is constructed as a disposable part which is coupled together with hoses 11 and 12, which are likewise made from plastic, and with a valve made from simple plastic components.

Figure 2:
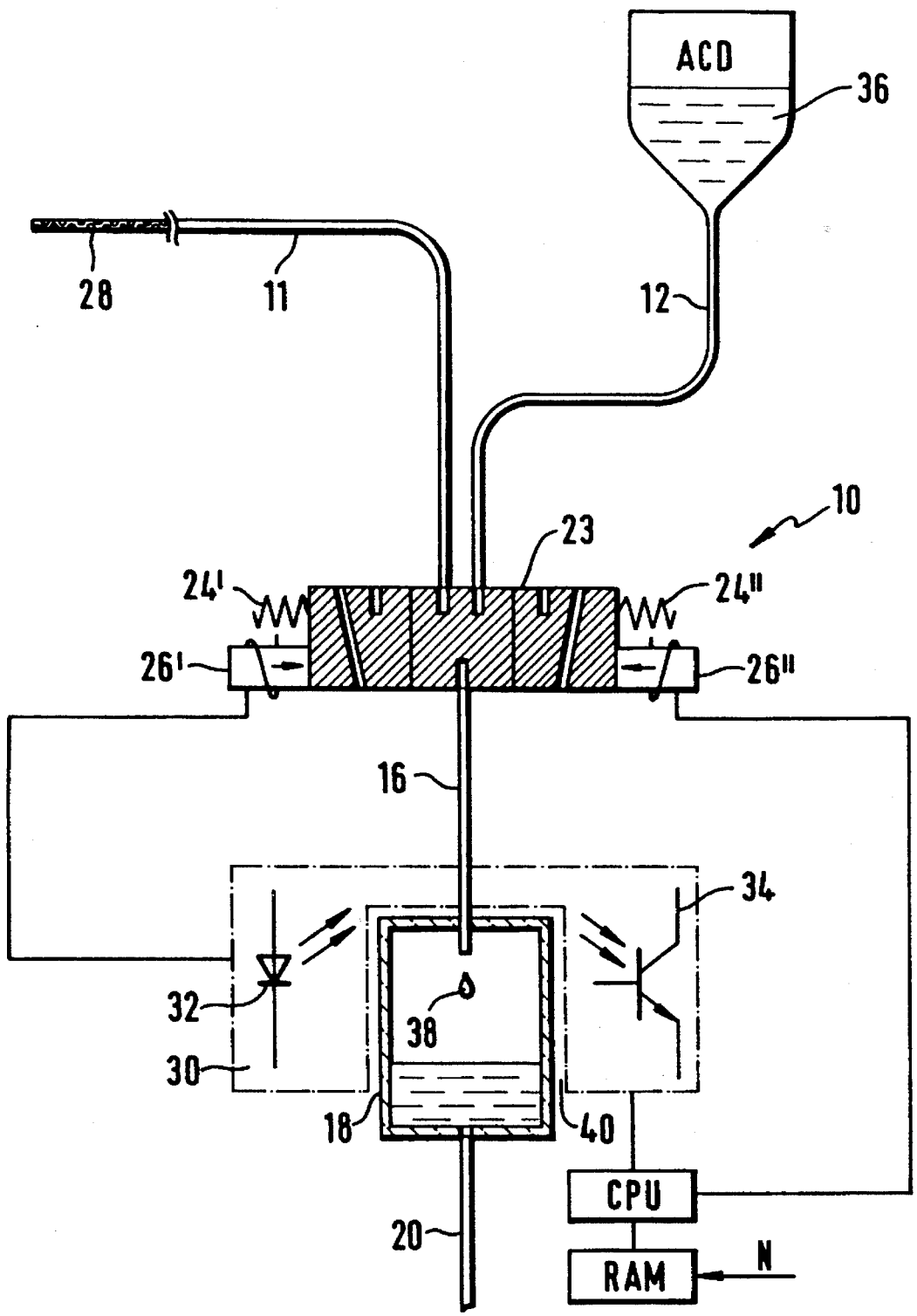
FIG. 2 is a schematic representation of a second version of a dosing device according to the invention.

An alternative embodiment of the dosing device according to the present invention is shown in FIG. 2, wherein a 3/3-way valve is used in place of a 4/2-way valve. The other components and elements correspond to the version shown in FIG. 1, the same parts having the same reference numbers so that their description need not be repeated.

The 3/3-way valve 23 in FIG. 2 has two compression springs 24' and 24", by means of which the valve is centered in the middle. In the represented resting position of the 3/3-way valve 23, both the hose line 11 and the hose line 12 are blocked so that no fluid whatsoever can reach the drip tube connected to the third connection of the 3/3-way valve. In operation, a switching signal is generated by the CPU which, suitably intensified, is fed to a first solenoid 26', so that the 3/3-way valve 23 is switched into a first engaged position, in which the drainage line or hose line 11 is connected to the drip tube 16, while the hose line 12 conveying the anticoagulant liquid still remains blocked. In this version of the invention, the two hose lines 11 and 12 are thus not coupled directly to one another at a junction, but are connected indirectly to one another via the 3/3-way valve 23. After a fixed number N the CPU generates a new switching pulse which, suitably amplified, is this time fed to the solenoid 26, whereupon the 3/3-way valve is pressed into a second engaged position in which the hose line 12 is connected to the drip tube 16 so that a further falling drop 38 draws anticoagulant liquid into the drip tube 16.

With reference to FIG. 2, it is evident that the dosing device according to the present invention can also be realized with a 3/2-way valve. If one imagines FIG. 2 without the middle, spring-centered resting position of the 3/3-way valve, then two engaged positions of a 3/2-way valve remain. In such a version or embodiment, the compression spring 24" and the left-hand solenoid 26' would not be present, with the result that the remaining compression spring 24' presses the 3/2-way valve into a resting position in which the hose line 11 is connected to the drip tube 16. After a corresponding number of fallen drops N, the CPU generates a corresponding switching pulse which is used to apply an exciting current to the solenoid 26", so that the 3/2-way valve is switched to an engaged position in which the hose line 12 conveying the anticoagulant liquid is connected to the drip tube 16.

As is also shown in the figures, the light barrier 30 is incorporated in a housing which has a channel-type recess 40. The correspondingly constructed drip chamber 18 can be locked in form-locking manner into this recess 32. The discharge line 20, the drip chamber 18, the drip tube 16, the valves 22 and 23, and the two hose lines 11 and 12 can be constructed as disposable parts which can be simply replaced when the device, i.e. the parts to be reused, such as in particular light barrier 30, CPU and RAM, are to be used for example in another operation.

The dosing device according to the present invention permits an accurate volumetric metered addition of an additive without a changing drop size of drops detected and counted by means of a light barrier having an influence on the accuracy of the dosing.

What is claimed is:

1. A dosing device for volumetric dosing of a liquid additive which is added in a certain volume ratio to a fluid flowing in two hose lines comprising a first hose line and a second hose line which feeds directly or indirectly into the first hose line, said dosing device comprising two electrically triggerable valve means which are each inserted into one of two hose lines and coupled so that only one of the two valve means is switched in a switching cycle to an open position; a counting and control unit (CPU, RAM); a drip tube which extends downstream from a junction; a drip chamber connecting downstream from the drip tube; and a light barrier, the direction of action of which is arranged transversely to a fall path of drops of additive, whereby drops falling in the drip chamber are counted and the valve means is alternately triggered by the counting and control unit after a certain number of drops have been counted.

2. A dosing device according to claim 1, wherein the two valve means comprise a 4/2-way valve.

3. A dosing device according to claim 1, wherein the two valve means comprise a 3/2-way valve.

4. A dosing device according to claim 2 wherein the 4/2-way valve is spring-loaded, and the first hose line is switched to the open position in a resting position.

5. A dosing device according to claim 1, wherein the valve means comprise a 3/3-way valve which has a spring-centered middle position in which the two hose lines are blocked.

6. A dosing device according to claim 1, wherein the counting and control unit comprises a freely programmable memory (RAM), inputting means for entering a value (N) representing a number of drops, and a central processing unit (CPU) for generating a control pulse for alternate triggering of the valve means when an ascertained number of the drops reaches the value (N) stored in the freely programmable memory (RAM).

7. A dosing device according to claim 1, wherein the counting and control unit comprises a freely programmable memory (RAM) in which there is provided a memory space for a constant (A) which corresponds to the number of drops of additive to be added per switching cycle of the valve means.

8. A dosing device according to claim 1, wherein the counting and control unit comprises a central processing unit (CPU) and a freely programmable memory (RAM) in which an operating program for the processing unit is stored which controls the valve means alternately so that after a certain number of switching cycles of the valve means, a switching cycle is carried out in which the second hose line conveying the additive is switched through until the volume of additive which has flowed out, as determined by the light barrier, corresponds substantially to the volume of the drip tube and any dead spaces in the valve means.

9. A dosing device according to claim 1, wherein the two hose lines, the two valve means, the drip tube, and the drip chamber comprise disposable parts.

10. A dosing device according to claim 9, wherein the drip chamber and the light barrier are constructed such that the drip chamber constructed as a disposable part can be locked in the correspondingly constructed light barrier.

11. A dosing device according to claim 10, wherein the drip chamber is lockable in a form-locking manner with a component comprising the light barrier.

* * * * *